United States Patent [19]

Ellis

[11] Patent Number: 5,171,248

[45] Date of Patent: Dec. 15, 1992

[54] MEDULLARY CALIPER

[75] Inventor: John G. Ellis, Austin, Tex.

[73] Assignee: Intermedics Orthopedics, Inc., Austin, Tex.

[21] Appl. No.: 661,804

[22] Filed: Feb. 27, 1991

[51] Int. Cl.[5] ............................................. A61F 5/04
[52] U.S. Cl. .................................... 606/102; 128/774; 33/512; 33/542.1; 33/558.4
[58] Field of Search ...................... 606/102, 63; 33/511, 33/512, 542, 542.1, 558.01, 558.04, 558.4, 783, 806, 807; 128/774, 775, 778

[56] References Cited

U.S. PATENT DOCUMENTS

| | | | |
|---|---|---|---|
| 3,352,021 | 11/1967 | Leach et al. | 33/542 |
| 4,016,867 | 4/1977 | King et al. | 128/778 |
| 4,362,167 | 12/1982 | Nicolai et al. | 128/778 |
| 4,536,960 | 8/1985 | Muti | 33/783 |
| 4,982,505 | 1/1991 | Pocci | 33/542 |

OTHER PUBLICATIONS

Sweet, "Expansion Gage Checks Internal Protected Holes", *American Machinist*, Dec. 25, 1950, p. 122.

Primary Examiner—Randy C. Shay
Attorney, Agent, or Firm—John R. Merkling

[57] ABSTRACT

An medullary caliper comprising a sleeve or tube with internally actuated caliper arms at a distal end thereof. The sleeve is graduated so that the depth at which a measurement is being taken can be immediately determined. A control rod extends the caliper arms radially outward within the medullary canal to perform the measurement. Displacement of the control rod is translated by a scale into a direct reading of the diametric dimension of the medullary canal.

12 Claims, 2 Drawing Sheets

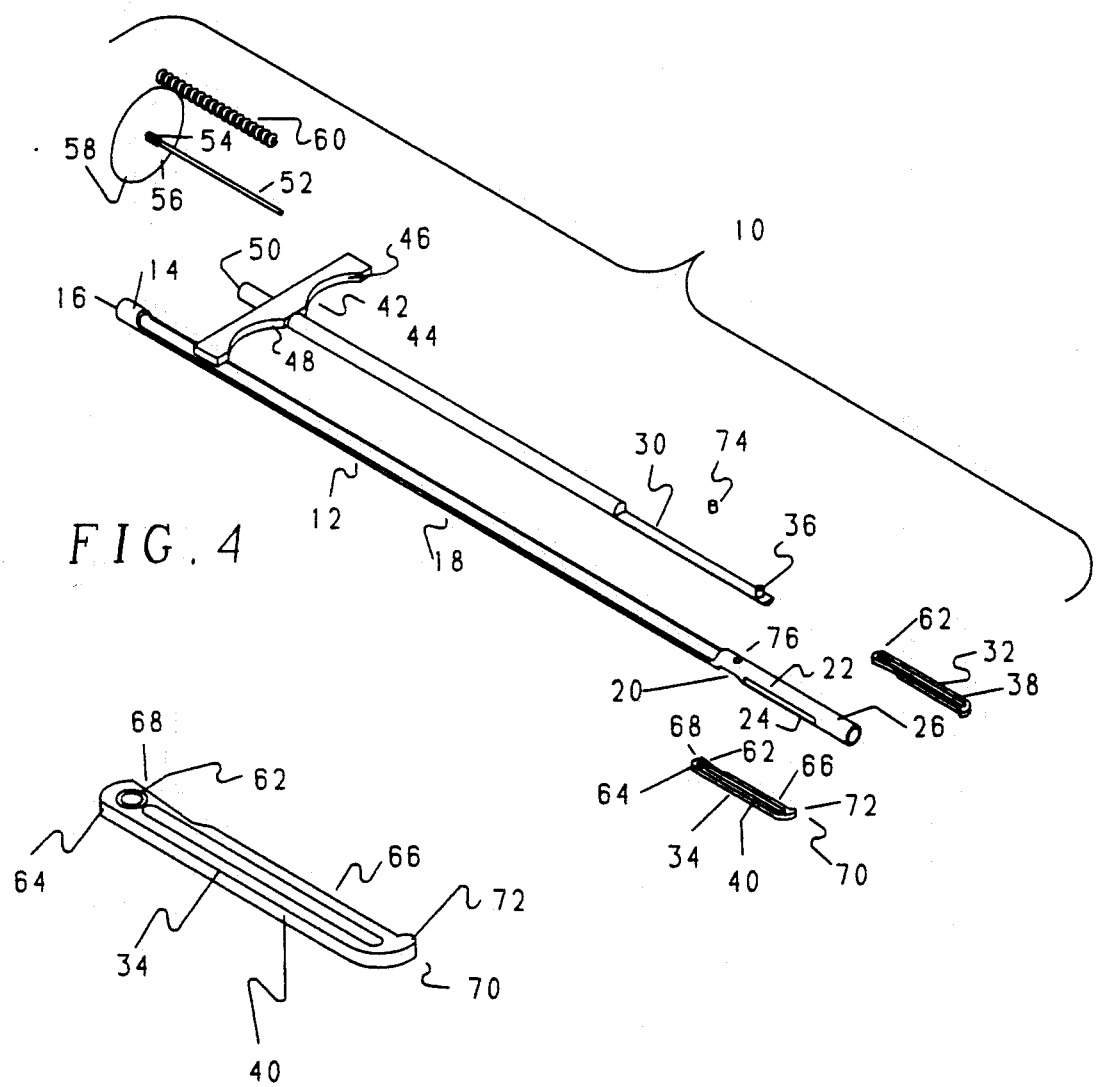

MEDULLARY CALIPER

BACKGROUND OF THE INVENTION

My invention is in the field orthopedic surgical guides and jigs. Specifically, I have invented an medullary caliper for use in connection with the implantation of prosthetic joints.

In the field of orthopedic prostheses, diseased or injured natural joints are replaced with prosthetic devices. Joints in the hip, knee, shoulder, elbow, ankle and fingers have been replaced with prostheses. Such prostheses are secured to adjacent bone by a number of known means. Such means include bone screws, pegs or other securing devices which may be used alone or in combination. One of the means frequently employed is a shaft or stem which is extends into the medullary canal of the adjacent bone. This is the method most frequently used in replacing a defective head for a femur in a hip prosthesis, but the means has also been used in prosthetic knees, fingers and shoulders. To implant such a prosthesis, a portion of the joint is cut away, exposing a resected surface of the bone. A cavity is reamed into the bone to receive the prosthesis and the prosthesis is placed into the reamed cavity with the stem extending into the medullary canal. The prosthesis is secured against lateral movement by a combination of features such as bone cement, distal spacers on the end of the stem of the prosthesis, or auxiliary sleeves placed on the stem of the prosthesis. Distal spacers are known, for example from Lee, U.S. Pat. No. 4,753,657 or Ling, U.S. Pat. No. 3,793,650. Sleeves have been used in the so-called Whiteside Hip produced by Dow Corning Wright. Another type distal size means has been disclosed by Averill in U.S. Pat. No. 4,770,660. Each of these distal stem features provide means for altering the size of a prosthesis to meet the particular physiological requirements of a patient. The effective use of such features depends on the fit achieved between the distal feature of the prosthetic stem and the medullary canal. It is, therefore, important for a surgeon to know, as accurately as possible, the diametric dimension of the medullary canal at the location where the distal feature will be employed.

In the past, surgeons have relied on their general experience or have attempted to estimate the size of an medullary canal from x-ray photographs. Neither of these methods is reliably accurate. X-ray photography, for example, does not provide a fixed scale nor is it immediately clear that all features in such a photograph reside in any given plane. It is, therefore, very difficult to get an accurate measurement of absolute size from a an x-ray photograph.

It is an object of my invention, therefore, to provide an apparatus for measuring diametrical dimensions of an medullary canal.

It is a further object of my invention, to provide such an apparatus which can give accurate multiple readings at selected depths within the medullary canal.

Another object of my invention is to provide an apparatus which can provide Medullary measurements in multiple selected directions.

A further object of my invention is to provide a caliper which can be used by a surgeon during a surgical procedure to accurately size distal features of a prosthesis.

SUMMARY OF MY INVENTION

I have invented an medullary caliper comprising a sleeve or tube with internally actuated caliper arms at a distal end thereof. The sleeve is graduated so that the depth at which a measurement is being taken can be immediately determined. A control rod extends the caliper arms radially outward within the medullary canal to perform the measurement. Displacement of the control rod is translated by a scale into a direct reading of the diametric dimension of the medullary canal.

These and other features and objects of my invention will be apparent to those skilled in the art from the following detailed description, taken with reference to the accompanying drawings.

BRIEF DESCRIPTION OF THE DRAWINGS

FIG. 4 is an exploded perspective view of the caliper of FIG. 1.

FIG. 5 is an enlarged perspective view of a caliper arm.

DETAILED DESCRIPTION OF MY PREFERRED EMBODIMENT

Figure 1:
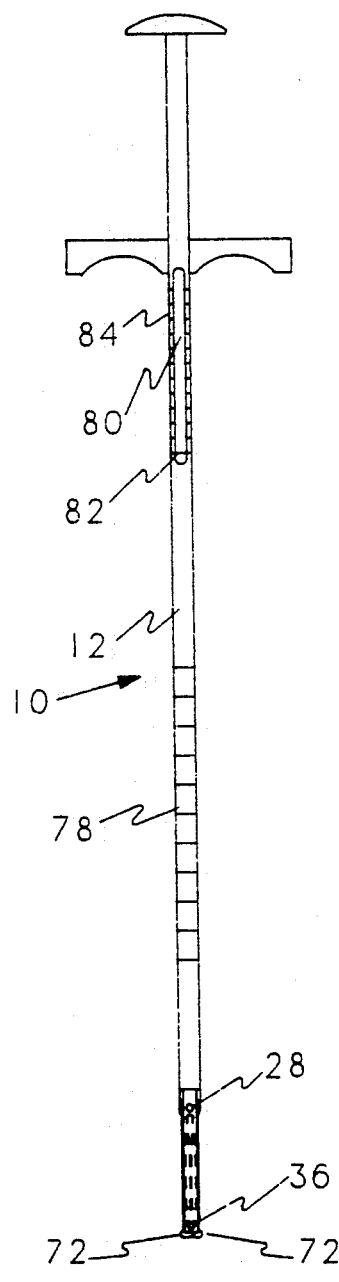
FIG. 1 is a plane view of a medullary caliper according to my present invention showing caliper arms in a closed position.

I will now described my preferred embodiment of my invention by reference to the accompanying drawings. Like numerals will refer to like parts in each drawing. The component parts of my invention can best be understood by reference to the exploded perspective view of FIG. 4.

In FIG. 4, an exploded, perspective view of a caliper, generally labeled 10, is shown. The medullary caliper 10 comprises an elongated member, preferably a sleeve, 12 which contains and supports the other elements of the caliper. The sleeve 12 is essentially a thin wall tube with a threaded segment 14 at a proximal end 16. A middle portion 18 of the sleeve 12 is cut away, exposing the interior of the sleeve. A smaller cut away 20 is provided near a distal end 22 of the sleeve 12 for access to other parts the caliper. Two opposed slots 24, 26 are also provided in the distal end of the tube. A rod 28 slides in the interior of the sleeve 12. The rod 28 has a cut away distal tip 30 for manipulating two caliper arms 32, 34. A pin 36 is affixed at the distal end of the rod 28 and engages slots 38, 40 in the caliper arms 32, 34, respectively. A grip 42 is provided at a proximal end 44 of the rod 28. In my preferred embodiment, the grip 42 is configured symmetrically about the rod 28 with curved distal sides 46, 48, adapted to be manipulated with a surgeon's index and middle fingers. In the proximal end 44 of the rod 28 there is a concentric bore 50. A stabilizer rod 52 slides in the bore 50 to hold the rod 28 within the sleeve. The stabilizer rod 52 has external threads 54 at a proximal end 56 and a palm rest 58 adjacent the threads 54. The stabilizer rod is adapted to slide into the proximal end 16 of the sleeve 12 and engage the concentric bore 50 in the rod 28. As the stabilizer rod 52 is inserted into the sleeve 12, a coiled spring 60 is placed in the sleeve 12 and the stabilizer rod is threaded therethrough. The stabilizer rod 52 is then screwed into the proximal end 16 of the sleeve 12. The coiled spring 60 forces the rod 28 distally within the sleeve 12.

The two caliper arms 32, 34 are mirror images of each other so that the description of one caliper arm, for example, caliper arm 34, suffices for both. The caliper arm 34 comprises the slot 40 extending along the length of the arm and a pivot hole 62 at a proximal end 64 of the arm 34. On an exterior side 66 at the proximal end 64, there is a cut away 68 which permits the arm 34 to be exposed outside the sleeve 12 to a greater extent than would be otherwise be possible. On the same exterior side 66 at a distal end 70, a lateral tip 72 extends from the arm 34. The lateral tip 72 is the part of the caliper which is intended to actually make contact with interior wall of the medullary canal to provide measurement. The caliper arms 32, 34 are stacked one above the other on the distal end 30 of the rod 28 with the pin 36 engaging both slots 38, 40. The rod 28 and caliper arms 32, 34 are then placed in the sleeve 12 and a pin 74 is passed through a bore 76 in the distal end of the sleeve, and through the pivot holes 62 in the caliper arms. The caliper arms rotate around the pin 74 as they are displaced by the motion of the pin 36 in the slots 38, 40.

Figure 2:
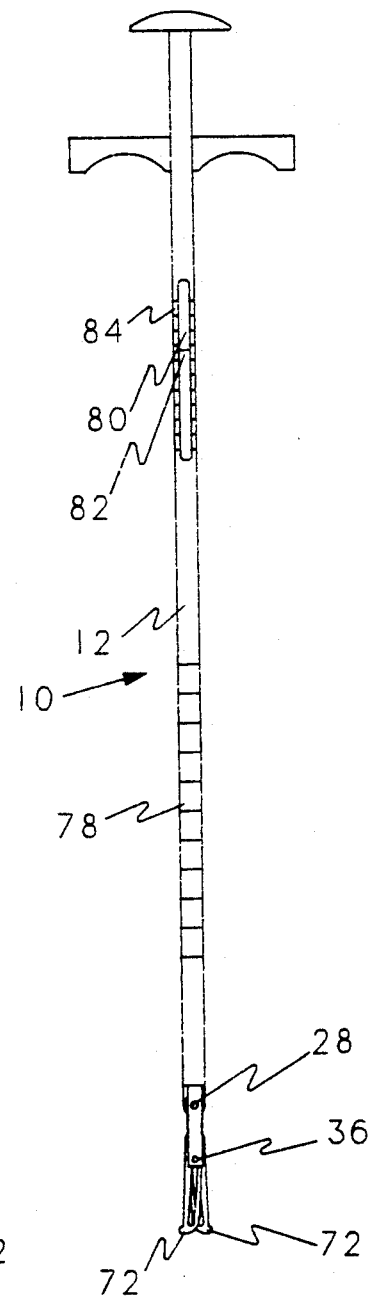
FIG. 2 is a plane view of the caliper of FIG. 1 showing the caliper arms in partially extended position.
Figure 3:
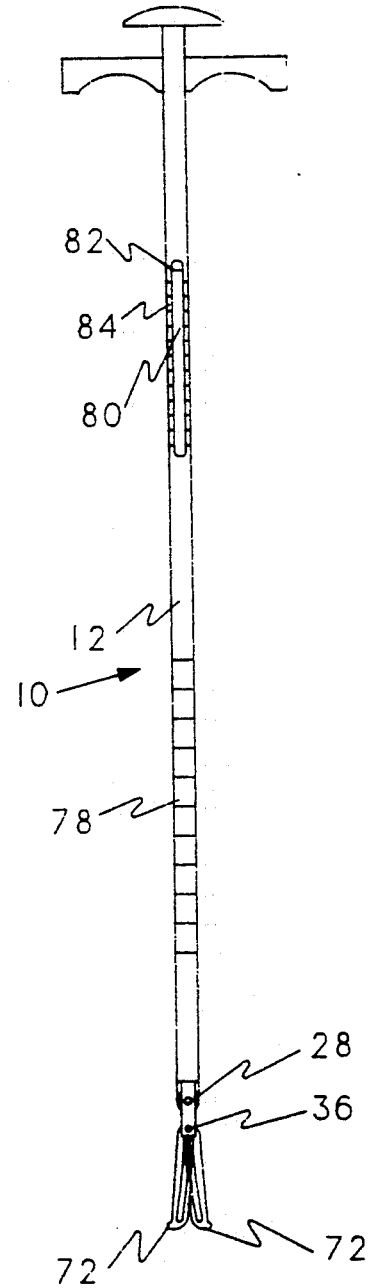
FIG. 3 is a plane view of the caliper FIG. 1 showing the caliper arms in fully extended position.

This action can be understood with reference to FIGS. 1, 2 and 3. In these figures, plane bottom views of the caliper 10 are shown. For clarity, the distal tip 22 of the sleeve 12 is not shown. As shown in FIGS. 1 through 3, the slots 38, 40 are curved with a center curvature on the side of the caliper towards which the respective arm will be extended. In FIG. 1, the caliper 10 is shown is closed position. A depth scale 78 is scribed on the sleeve 12. This scale permits the surgeon to immediately read the depth to which the caliper is inserted into the medullary canal. A viewing slot 80 in the sleeve 12 provides a view of the rod 28 and particularly of mark or groove 82 on the rod 28. A diameter scale 84 on the sleeve 12 permits a surgeon to read the diameter of the medullary canal from the alignment of between of the groove 82 and the scale 84.

As seen in FIG. 1, when the caliper arms are closed, the rod 28 is displaced distally so that the pin 36 is at a distal end of the slots 38, 40. The lateral tips 72 of the caliper arms are at their closest approach to each other. As a surgeon begins to draw on the grip 42, the rod 28 is displaced proximally as can be seen in FIG. 2, drawing the pin 36 along the slots 38, 40 in the caliper arms and displacing the lateral tips 72 outward. This process can be continued until pin 36 reaches a proximal end of the slots 38, 40 and the lateral tips 72 are at their maximum displacement from each as shown in FIG. 3.

Using the calipers of my invention, the surgeon can make rapid multiple measurements of the size of an medullary canal during a surgical procedure at different selected depths and orientations. An irregular shape of the canal can be rapidly determined and an appropriate distal tip or sleeve can be chosen for the particular prosthesis being used by the surgeon.

My invention may be embodied in other specific forms without departing from the spirit or essential characteristics thereof. The scope of my invention is to be defined by the appended claims, and not by the foregoing description, and all changes which come within the meaning of equivalency of the claims are intended to be encompassed therein.

I claim as my invention:

1. A caliper for measuring a diametrical dimension of a medullary canal in a bone of a patient, the caliper comprising an elongated member for insertion into the medullary canal, said elongated member having a distal end and a proximal end, adjustable means carried within the distal end of the elongated member for selectively engaging walls of the medullary canal and displacable laterally outside of said elongated member, said adjustable engaging means comprising at least one caliper arm pivotally connected to said elongated member at the distal end of said elongated member, a rod slidably engaging said at least one caliper arm, said rod connected to the adjustable engaging means for controlling the position of the adjustable means with respect to the elongated member, scale means associated with the control means for displaying the position of the adjustable engaging means, and depth scale means for displaying the extent of insertion of the elongated member into the medullary canal.

2. The caliper according to claim 1 wherein the caliper arm has a curved slot therein, and said rod engages said slot.

3. The caliper according to claim 2 wherein the adjustable engaging means comprise two opposed caliper arms, each arm pivotally connected to said elongated member and slidably connected to said rod.

4. The caliper according to claim 3 wherein the elongated member comprise a sleeve.

5. A caliper for measuring a diametrical dimension of a medullary canal in a bone of a patient, the caliper comprising an elongated member for insertion into the medullary canal, said elongated member having a distal end and a proximal end, adjustable means carried within the distal end of the elongated member for selectively engaging walls of the medullary canal and displacable laterally outside of said elongated member, said adjustable engaging means comprising at least one caliper arm pivotally connected to said elongated member at the distal end of said elongated member, a rod slidably engaging said at least one caliper arm, said rod connected to the adjustable engaging means for controlling the position of the adjustable means with respect to the elongated member.

6. The caliper according to claim 1 wherein the caliper arm has a curved slot therein, and said rod engages said slot.

7. The caliper according to claim 6 wherein the adjustable engaging means comprise two opposed caliper arms, each arm pivotally connected to said elongated member and slidably connected to said rod.

8. The caliper according to claim 7 further comprising scale means associated with the control means for displaying the position of the adjustable engaging means.

9. The caliper according to claim 8 further comprising depth scale means for displaying the extent of insertion of the elongated member into the medullary canal.

10. A caliper for measuring an internal dimension of a medullary canal of a bone of a patient, said caliper comprising a sleeve adapted to be inserted into the medullary canal, said sleeve having a distal end and a proximal end;

a rod slidably received within said sleeve, said rod having a distal end and a proximal end;

means connected to the proximal end of said rod for displacing the rod within the sleeve;

at least two opposed caliper arms, each caliper arm having a distal end and a proximal end, the proximal end of each caliper arm being pivotally connected to said sleeve near the distal end thereof and each caliper arm having a curved slot therein and being slidably connected at said slot to said rod near the distal end thereof; and tip means at the distal end of each caliper arm for engaging adjacent walls of the medullary canal, whereby an interior diametral dimension of said medullary canal can be measured by displacing the rod with respect to the sleeve.

11. The caliper according to claim 10 further comprising scale means carried on said sleeve and on said rod for measuring the displacement of the rod with respect to the sleeve.

12. The caliper according to claim 11 further comprising insertion scale means for measuring the extent of insertion of the caliper into the medullary canal.

* * * * *